United States Patent [19]

Connor et al.

[11] Patent Number: 5,155,110

[45] Date of Patent: Oct. 13, 1992

[54] FENAMIC ACID HYDROXAMATE DERIVATIVES HAVING CYCLOOXYGENASE AND 5-LIPOXYGENASE INHIBITION

[75] Inventors: David T. Connor, Ann Arbor, Mich.; Daniel L. Flynn, Mundelein, Ill.

[73] Assignee: Warner-Lambert Company, Morris Plains, N.J.

[21] Appl. No.: 248,204

[22] Filed: Sep. 26, 1988

Related U.S. Application Data

[63] Continuation-in-part of Ser. No. 134,725, Dec. 18, 1987, abandoned, which is a continuation-in-part of Ser. No. 113,789, Oct. 27, 1987, abandoned.

[51] Int. Cl.$^5$ .................. C07C 259/10; A61K 31/27
[52] U.S. Cl. .................. 514/258; 514/418; 514/507; 514/575; 544/285; 544/287; 548/483; 560/315; 562/622
[58] Field of Search .......... 562/622, 440; 548/483; 544/286, 285; 514/507, 258, 418, 575; 560/312, 315

[56] References Cited

U.S. PATENT DOCUMENTS

| | | | |
|---|---|---|---|
| 4,029,815 | 6/1977 | Sherlock | 562/622 |
| 4,906,667 | 3/1990 | Varma | 514/575 |

FOREIGN PATENT DOCUMENTS

| | | |
|---|---|---|
| 0196184 | 10/1986 | European Pat. Off. |
| 0196674 | 10/1986 | European Pat. Off. |
| 2457867 | 4/1964 | Japan . |
| 24578 | 11/1967 | Japan . |
| 989951 | 4/1965 | United Kingdom . |

OTHER PUBLICATIONS

Wolf and Kohn; Liebigs Ann. Chem. 1975, 1245-1251 "Cyclisierungsreaktionen von am Aminostickstoff Substituierten o-Aminobenzhydroxamsaure-O-methylestern".

James B. Summers, et al., "Hydroxamic Acid Inhibitors of 5-Lipoxygenase" J. Med. Chem 1987, 30, 574-580.

Summers, et al. "In Vivo Characterization of Hydroxamic Acid Inhibitors of 5-Lipoxygenase" Sep. 1987, (Abstract).

*Primary Examiner*—Robert Gerstl
*Attorney, Agent, or Firm*—Ronald A. Daignault; Joan Thierstein

[57] ABSTRACT

The present invention is novel selected hydroxamic acid derivatives of fenamic acids having 5-lipoxygenase and cyclooxygenase inhibiting properties, pharmaceutical compositions for treating conditions advantageously affected by the inhibition and methods for treating these conditions in mammals, including humans suffering therefor.

17 Claims, No Drawings

FENAMIC ACID HYDROXAMATE DERIVATIVES HAVING CYCLOOXYGENASE AND 5-LIPOXYGENASE INHIBITION

This application is a continuation-in-part of U.S. application Ser. No. 134,725, filed Dec. 18, 1987, which is a continuation-in-part of U.S. application Ser. No. 113,789, filed Oct. 27, 1987, both now abandoned.

BACKGROUND OF THE INVENTION

The present invention is novel derivatives of fenamic acids. Such fenamic acids include mefenamic acids of U.S. Pat. No. 3,138,636; flufenamic acids of U.S. Pat. No. 3,144,387 meclofenamate and tolfenamic acids of U.S. Pat. No. 3,313,848; and niflumic acids, flunixin, and olonixin of U.S. Pat. No. 26,655.

Other anthranilic acid derivatives of the fenamic series previously known include the generic compounds of the British Patent No. 989,951 or formula

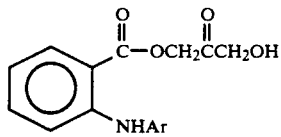

wherein Ar is α,α,α-trifuoro-m-tolyl; 2,3-xylyl; or 2,6-dichloro-m-tolyl, in U.S. Pat. No. 3,852,333.

The present novel derivatives include selected hydroxamic acids thereof which are heretofore unknown.

Among related aminobenzhydroxamic acids previously disclosed are compounds of the formula

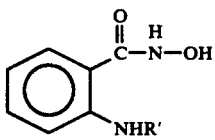

wherein R' is a saturated fatty hydrocarbon radical; phenyl, phenylalkyl, wherein the rings are optionally substituted by lower alkyl or lower alkoxy; or an aromatic heterocyclic group. This disclosure is in Japanese Application 24578/67, filed Apr. 2, 1964 by the Takeda Chemical Industry Co., Ltd. as an o-aminobenzhydroxamic acid analgesic derivative having less toxicity and analgesic, anticatarrhic, and antifebrile activity.

Other related disclosures include U.S. Pat. No. 4,029,815 to compounds of the formula

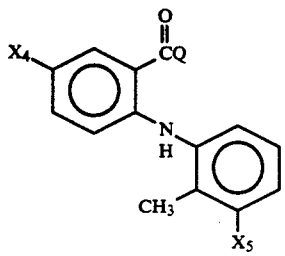

wherein $X_5$ is trifluoromethyl, difluoromethyl, or nitro, $X_4$ is H, Br, Cl, or nitro, and Q may be NHOH. These compounds have utility as antidiarrheal agents.

Cyclized o-aminobenzhydroxamic-O-methylesters of the formula

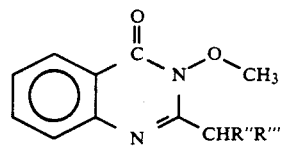

wherein R" is alkyl, aralkyl, or a basic side chain and R''' is H, Cl, or Br; are disclosed by Wolf, E. and Kohl, H. in "Cyclisiarungareaktionen von am Aminostickstoff Substituierten o-Aminobenz-hydroxamsaure-O-methylesteror," *Ann. Chem. Liebigs,* 1975, 1245–1251.

Wolf and Kohl also disclose an intermediate hydroxamic acid derivative from which the cyclized o-aminobenzhydroxamic-O-methylesters are made. The intermediate is

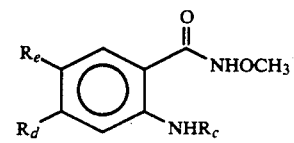

wherein $R_c$, $R_e$, and $R_d$ are as defined below.

Other cyolized o-aminobenzyhydroxamic acids disclosed are

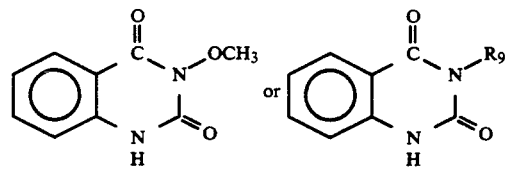

wherein $R_a$ is $CH_2CO_2C_2H_5$, $C_6H_3Cl(p)NO_2(m)$ and suggesting that $R_a$ may also be $SO_2C_6H_4CH_3(p)$; and

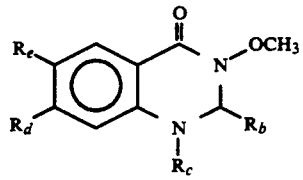

wherein $R_b$ is H or phenyl; $R_c$ is H, $CH_2C_6H_5$, $C_6H_4Cl(p)$, $CH_2C_6H_4Cl(p)$, $C_6H_5$, or $CH_3$; $R_e$ is H or $NO_2$; and $R_d$ is H or Cl. However, Wolf and Kohl do not disclose activity for these cyclized compounds and, further, do not make obvious the present invention.

Broadly, hydroxamic acid derivatives of selected aryl ring systems are disclosed in European Application Publication No. 0 196 184 having surprisingly high potency particularly by inhalation, oral efficacy, and with a surprisingly long duration of action. However, these aryl ring systems are in no way related to the present fenamic acid type compounds.

Two disclosures by Summers et al, (1) *J. Med. Chem.,* 1987, 30, 574–80 and (2) In Vivo Characterization of Hydroxamic Acid Inhibitors of 5-Lipoxygenase disclosed at a seminar in early September, 1987 (Abstract) disclose hydroxamic acids as inhibitors of 5-lipoxygenase, however, the disclosures do not extend beyond very limited representative examples not including any fenamic acid derivatives.

Additional references related to the present invention, particularly for the substituents therein for $L_1$ and $L_2$, include a disclosure for reduction of the substituent in the carboxy-containing side chain of anilinophenyl group in J55013-227 of Derwent Abstract No. 17678C/10; and various fused nitrogen-containing ring systems in J54151-963 in Derwent Abstract No. 02846C/02, J54073-771 in Derwent Abstract No. 55094B/30, J54073-750 in Derwent Abstract No. 550855/30, J54073-737 in Derwent Abstract No. 55078B/30, J54070-265 in Derwent Abstract No. 51907B/28, J54063-073 in Derwent Abstract No. 48163B/26, J54063-042 in Derwent Abstract No. 48147B/26, DL-134-520 in Derwent Abstract No. 39059B/21, and JA2489/67 in Derwent Abstract No. 29861, U.S. Pat. No. 3,325,499 in Derwent Abstract No. 27,108 and 3,317,524 in Derwent Abstract No. 26,495.

Also in CA73(2):10333g 1-phenyl-3-isatinoxime is disclosed. The compounds disclosed in each of these references is not now the present invention because the particular substituents noted as $L_1$ and $NOR_7$ found in the present invention are not included or made obvious from the references.

Thus, the present invention are to selected novel derivatives of fenamates and pharmaceutically acceptable acid addition or base salts thereof, pharmaceutical compositions for treating inflammation, arthritis, pain, pyrrhia, and the methods for such treatment.

Finally, known related cyclized compounds include the quinazolinedione derivatives disclosed in U.S. Pat. No. 3,794,643 which are different from the present cyclized derivatives by unobvious substituents, particularly at the nitrogen between the carbonyls.

SUMMARY OF THE INVENTION

The present invention is a novel compound of the formula (I)

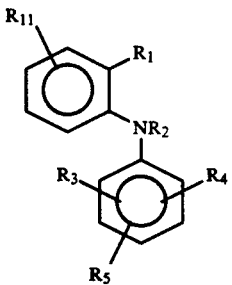

I wherein
(1) $R_1$ is (i)

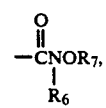

(ii)

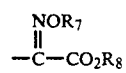

wherein $R_6$ is hydrogen, lower alkyl, aryl, aralkyl, or cycloalkyl of from three to ten carbons having three to seven ring carbons; $R_7$ is independently H, lower alkyl, or acyl; and $R_8$ is H or lower alkyl; with the proviso that when $R_1$

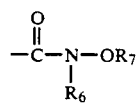

$R_7$ cannot be methyl when $R_5$ is para-chloro and $R_3$ and $R_4$ are hydrogen, and (iii) as defined together with $R_2$ below;

(2) —$R_2$ is H, lower alkyl, or taken together with —$R_1$ is

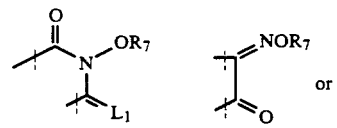

or wherein $L_1$ is oxygen or $H_2$; and $R_7$ is independently as defined above; and (3) $R_3$, $R_4$, $R_5$, and $R_{11}$ are independently hydrogen, fluoro, chloro, bromo, trifluoromethyl, lower alkyl, CN, hydroxy, lower alkoxy, —S(O)$_n$-lower alkyl, NO$_2$, or NR$_9$R$_{10}$ wherein $R_9$ and $R_{10}$ are independently H, lower alkyl, or acyl and n is an integer of 0 through 2, with the further proviso that when $R_1$ is

CNHOH then $R_3$, $R_4$, or $R_5$ cannot all be hydrogen or then one or two of $R_3$, $R_4$, or $R_5$ cannot be alkyl when the other one or two of $R_3$, $R_4$, or $R_5$ is hydrogen, and when $R_1$ is

CNHOH and one of $R_3$, $R_4$, or $R_5$ is ortho-alkyl then one other of $R_3$, $R_4$, or $R_5$ cannot be meta-nitro, meta-difluoromethyl, or meta-trifluoromethyl when $R_{11}$ is H, Br, Cl, or nitro and pharmaceutically acceptable acid addition or base salts thereof.

The present invention is also a pharmaceutical composition for the treatment of conditions advantageously affected by the inhibition of 5-lipoxygenase and/or cyclooxygenase which comprises administering an amount effective for inhibiting 5-lipoxygenase and/or cyclooxygenase of a novel compound of the formula (I)

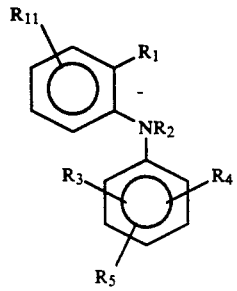

I wherein
(1) $R_1$ is

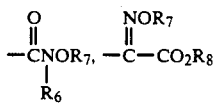

wherein $R_6$ is hydrogen, lower alkyl, aryl, aralkyl, or cycloalkyl of from three to ten carbons having three to seven ring carbons; $R_7$ is independently H, lower alkyl, or acyl; and $R_8$ is H or lower alkyl; and as defined together with $R_2$ below;

(2)

is H, lower alkyl, or taken together with

is

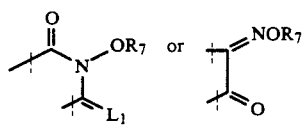

wherein $L_1$ is oxygen or $H_2$; and $R_7$ is independently as defined above; and (3) $R_3$, $R_4$, $R_5$, and $R_{11}$ are independently hydrogen, fluoro, chloro, bromo, trifluoromethyl, lower alkyl, CN, hydroxy, lower alkoxy, —$S(O)_n$-lower alkyl, $NO_2$, or $NR_9R_{10}$ or $NO_2$ wherein $R_9$ and $R_{10}$ are independently H, lower alkyl, or acyl; and n is an integer of 0 through 2; with the proviso that when $R_1$ is

then $R_3$, $R_4$, or $R_5$ cannot all be hydrogen or then one or two of $R_3$, $R_4$, or $R_5$ cannot be alkyl when the other one or two of $R_3$, $R_4$, and $R_5$ is hydrogen, and when $R_1$ is

and one of $R_3$, $R_4$, or $R_5$ is ortho-alkyl then one other of $R_3$, $R_4$, or $R_5$ cannot be meta-nitro, meta-difluoromethyl, or meta-trifluoromethyl when $R_{11}$ is H, Br, Cl, or $NO_2$; and pharmaceutically acceptable acid addition or base salts thereof and a pharmaceutically acceptable carrier.

Further, the present invention also provides a method of use for a composition of a compound of the formula (I), as defined herein before, or physiologically acceptable acid addition or base salt thereof for use as an inhibitor of the lipoxygenase and/or cyclooxygenase enzymes of the mammalian including human arachidonic acid metabolism, which method comprises inhibition of such enzymes by administration to a mammal of a ipoxygenase and/or cyclooxygenase inhibiting amount of any such compound or salt in unit dosage form, and to use of any such compound or salt in the manufacture of lipoxygenase and/or cyclooxygenase inhibitor agents.

Further, the present invention also provides any compound or composition of formula (I) (as hereinbefore defined) or physiologically acceptable salt thereof, for use as a medical therapeutic and/or prophylactic agent, to methods of medical therapeutic and/or prophylactic treatment by administration to a mammal of a medically therapeutic and/or prophylactic effective amount of any such compound or salt, and to use of any such compound or salt in the manufacture of medical therapeutic and/or prophyactic agents. The kinds of medical therapy and prophylaxis pertinent to the foregoing and therefore in that sense comprising part of the present invention, are elaborated by way of example in the following paragraphs which are not intended to be construed as in any way limiting the scope of these aspects of said invention.

The most preferred compound of the present invention is 1-(2,6-dichloro-3-methylphenyl)-2,3-dihydro-3-hydroxy-4(1H)-quinazolinone, which is shown in Example 35 hereinafter.

DETAILED DESCRIPTION OF THE INVENTION

In the compounds of formula (1) the term "lower alkyl" is meant to include a straight or branched alkyl group having one to four carbon atoms, such as, for example, methyl, ethyl, propyl, or butyl, and isomers thereof.

Lower alkoxy is O-alkyl or of from one to four carbon atoms as defined above for "lower alkyl".

Acyl is a

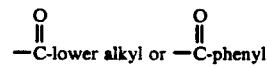

optionally substituted by a lower alkyl, fluoro, chloro, bromo, trifluoromethyl, hydroxy, or lower alkoxy; and wherein the lower alkyl is as defined above.

Cycloalkyl of from three to ten carbons having from three to seven ring carbons includes cyclopropyl, cyclobutyl, methylcyclotrityl, ethylcyclobutyl, dimethylcyclobutyl, cycopentyl, and the like.

Aryl is phenyl unsubstituted and substituted with from one to three substituents selected from the group consisting of hydroxy, lower alkoxy, fluoro, chloro, bromo, trifluoromethyl, lower alkyl, CN, —$S(O)_n$- lower akyl wherein n is as defined above, $NO_2$, or $NR_9R_{10}$ wherein $R_9$ and $R_{10}$ are independently as defined above.

An aralkyl is an aryl as defined above attached through a lower alkylenyl wherein the alkylenyl is of from one to four carbons such as methylenyl, 1,2-ethylenyl, 1,1-ethylenyl, propylenyl, and the like.

Appropriate compounds of formula (I) are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively or those derived from bases such as suitable organic and inorganic bases. Examples of pharmaceutically acceptable base addition salts with compounds of the present invention include organic bases which are nontoxic and strong enough to form such sats. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethy)-aminomethane; and the like. (See for example, "Pharmaceutical Salts," *J. Pharm. Sci.*, 66(1):1-19 (1977).) Salts of inorganic bases include sodium, potassium, calcium or the like.

The acid addition sats of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom. Thus, the invention includes the individual stereoisomers, and mixtures thereof. The individual isomers may be prepared or isolated by methods known in the art.

By virtue of their lipoxygenase inhibitory properties, said compounds and salts find application in the treatment and/or prophylaxis of any condition where a lipoxygenase inhibitor is indicated, especially spasmogenic and allergic conditions, psoriasis, and as utility in cytoprotection.

By virtue of their cycooxygenase inhibitory properties, said compounds and salts find application in the treatment and/or prophylaxis of any condition where a cyclooxygenase inhibitor is indicated, especially pyresis, pain, and inflammation.

By virtue of both their lipoxygenase and cyclooxygenase inhibitory properties, said compounds and salts find application in the treatment and/or prophylaxis of any condition where a dual lipoxygenase/cyclooxygenase inhibitor is indicated, especially any condition involving blood platelet aggregation or inflammation. In the case of inflammation, the compounds and salts are particularly suited to the treatment and/or prophylaxis of conditions associated with infiltration of leukocytes into inflamed tissue.

In determining when a lipoxygenase, cyclooxygenase, or dual lipoxygenase/cyclooxygenase inhibitor is indicated, of course inter alia, the particular condition in question and its severity, as well as, the age, sex, weight, and the like of the subject to be treated, must be taken into consideration and this determination is ultimately at the discretion of the attendant physician.

Examples of the aforesaid spasmogenic conditions are those involving smooth muscle tissue, especially airway smooth muscle constriction such as intrinsic asthma—(including intrinsic or idiopathic bronchial asthma and cardiac asthma), bronchitis and arterial smooth muscle constriction such as coronary spasm (including that associated with myocardial infarction, which may or may not lead to eft ventricular failure resulting in cardiac asthma) and cerebral spasm or 'stroke'. Other examples include bowel disease caused by abnormal colonic muscular contraction such as may be termed 'irritable bowel syndrome', 'spastic colon', or 'mucous colitis'.

Examples of the aforesaid allergic conditions are extrinsic asthma (from which it will be appreciated that said compounds and salts are particularly favorable as antiasthmatic agents), allergic skin diseases such as eczema having a total or partial allergic origin, allergic bowel disease (including coeliac disease) and allergic eye conditions such as hay fever (which may additionally or alternatively affect the upper respiratory tract) and allergic conjunctivitis. Examples of the aforesaid tumors are skin neoplasms, both benign and malignant.

Examples of the aforesaid pyretic and painful conditions include fever associated with infections, trauma and injury, malignant disease, and diseases affecting the immune system (including autoimmune diseases).

Examples of the aforesaid conditions involving blood platelet aggregation are those resulting from thrombosis, including 'stroke' having a total or partial thrombotic origin, coronary thrombosis, phlebitis, and phlebothrombosis (the latter two conditions also possibly being associated with inflammation).

Examples of the aforesaid conditions involving inflammation are inflammatory conditions of the lung, joints, eye, bowel, skin, and heart.

Inflammatory lung conditions which may be so treated and/or prevented include asthma and bronchitis (vide supra) and cystic fibrosis (which may also or alternatively involve the bowel or other tissue).

Inflammatory joint conditions which may be so treated and/or prevented include rheumatoid arthritis, rheumatoid spondylitis, osteoarthritis, gouty arthritis, and other arthritic conditions.

Inflammatory eye conditions which may be so treated and/or prevented include uveitis (including intis) and conjunctivitis (vide supra).

Inflammatory bowel conditions which may be so treated and/or prevented include Crohn's disease, ulcerative colitis, and ischemic bowel disease.

Inflammatory skin diseases which may be so treated and/or prevented include those associated with cell proliferation, such as psoriasis and eczema (vide supra) and dermatitis (whether or not of allergic origin).

Inflammatory conditions of the heart which may be so treated and/or prevented include coronary infarct damage.

Other inflammatory conditions which may be so treated and/or prevented include tissue necrosis of chronic inflammation and tissue rejection following transplant surgery.

It is also believed that the compound of formula (I) and their physiologically acceptable salts are effective agents in the prophylaxis and/or treatment of bacterial and fungal infections, thus forming a further aspect of the present invention in like manner.

For medical use, the amount required of a compound of formula (1) or physiologically acceptable salt thereof—(hereinafter referred to as the active ingredient) to achieve a therapeutic effect will, of course, vary both with the particular compound, the route of administration and the mammal under treatment and the particular disorder or disease concerned. A suitable dose of a compound of formula (I) or physiologically acceptable sat thereof for a mammal suffering from, or likely to suffer from any condition as described hereinbefore is 0.1 µg–500 mg of base per kilogram body weight. In the case of systemic administration, the dose may be in the range 0.5 to 500 mg of base per kilogram body weight, the most preferred dosage being 0.5 to 50 mg/kg of mammal body weight for Example 5 to 25 mg/kg; administered two or three times daily. In the case of topical administration, e.g. to the skin or eye, a suitable dose may be in the range 0.1 ng–100 µg of base per kilogram, typically about 0.1 µg/kg.

In the case of oral dosing for the treatment or prophylaxis of airway smooth muscle constriction, or asthma, or bronchitis in general, due to any course, a suitable dose of a compound of formula (I) or physiologically acceptable salt thereof, may be as specified in the preceding paragraph, but most preferably is from 1 mg to 10 mg of base per kilogram, the most preferred dosage being from 1 mg to 5 mg/kg of mammal body weight, for example from 1 to 2 mg/kg. In the case of pulmonary administration for the latter indications, the dose may be in the range of from 2 µg to 100 mg, for example from 20 µg to 0.5 mg, especially 0.1 to 0.7 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula (I) or a pharmacologically acceptable acid addition salt thereof and a physiologically acceptable acid addition salt thereof and a physiologically acceptable carrier therefor. Such formulations constitute a further feature of the present invention. Conveniently, the active ingredient comprises from 0.1% to 99.9% by weight of the formulation. Conveniently, unit doses of a formulation contain between 0.1 mg and 1 9 of the active ingredient. For topical administration, the active ingredient preferably comprises from 1% to 2% by weight of the formulation but the active ingredient may comprise as much as 10% w/w. Formulations suitable for nasal or buccal administration, (such as self-propelling powder dispensing formulations described hereinafter), may comprise 0.1 to 20% w/w, for example 2% w/w of active ingredient.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for intraarticular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intraarticular and ophthalmic administration.

Formulations suitable for topical administration include liquid or semi-liquid preparations such as liniments, lotions, applications, oil-in-water or water-in-oil emulsions such as creams, ointments or pastes; or solutions or suspensions such as drops. For example, for ophthalmic administration, the active ingredient may be presented in the form of aqueous eye drops as, for example, a 0.1–1.0% solution. Formulations suitable for administration to the nose or buccal cavity include powder, self-propelling and spray formulations such as aerosols and atomizers. The formulations, when dispersed, preferably have a particle size in the range of 0.1 to 200 µ.

A particularly valuable form of a pharmaceutical composition of the present invention, for use in the prophylaxis or treatment of airway smooth muscle constriction, or asthma or bronchitis in general, due to any cause, is one suitable for pulmonary administration via the buccal cavity. Preferably the composition is such that particles having a diameter of 0.5 to 7 µ, most preferably 1 to 6 µ, containing active ingredient, are delivered into the lungs of a patient. Such compositions are conveniently in the form of dry powders for administration from a powder inhalation device or self-propelling powder-dispensing containers, for example as a self-propelling aerosol composition in a sealed container; preferably the powders comprise particles containing active ingredient of which particles at least 98% by weight have a diameter greater than 0.5 μ and at least 95% by number have a diameter less than 7 μ. Most desirably at least 95% by weight of the particles have a diameter greater than 1 μ at least 90% by number of the particles have a diameter less than 6 μ.

The compositions in the form of dry powders preferably include a so]id fine powder diluent such as sugar and are conveniently presented in a permeable capsule, for example of gelatin.

Self-propelling compositions of the invention may be either powder-dispensing compositions or compositions dispensing the active ingredient in the form of droplets of a solution or suspension. Self-propelling powder-dispensing compositions include a liquid propellant having a boiling point of below 65° F. at atmospheric pressure. Generally the propellant may constitute 50 to 99.9% w/w of the composition whilst the active ingredient may constitute 0.1 to 20% w/w, for example about 2% w/w of the composition. The carrier in such compositions may include other constituents, in particular a liquid nonionic or solid anionic surfactant, or a solid diluent (preferably having a particle size of the same order as of the particles of active ingredient) or both. The surfactant may constitute from 0.01 up to 20% w/w, though preferably it constitutes below 1% w/w of the composition.

Self-propelling compositions wherein the active ingredient is present in solution comprise an active ingredient, propellant,. and co-solvent, and advantageously an antioxident stabilizer. The co-solvents may constitute 5 to 40% w/w of the composition, though preferably less than 20% w/w of the composition.

Compositions of the present invention may also be in the form of aqueous or dilute alcoholic solution, optionally a sterile solution, of the active ingredient for use in a nebulizer or atomizer.

Formulations of the present invention may also be in the form of an aqueous or dilute alcoholic solution, optionally a sterile solution, of the active ingredient for use in a nebulizer or atomizer, wherein an accelerated air steam is used to produce a fine mist consisting of small droplets of the solution. Such formulations usually contain a flavoring agent such as saccharin sodium and a volatile oil. A buffering agent and a surface active agent may also be included in such a formulation which should also contain a preservative such as methylhydroxybenzoate.

Other formulations suitable for nasal administration include a coarse powder having a particle size of 20 to 500 microns which is administered in the manner in which snuff is taken i.e., by rapid inhalation through the nasal passage from a container of the powder held close up to the nose.

In addition to the aforementioned ingredients, the formulations of this invention may include one or more additional ingredients such as diluents, buffers, flavoring agents, binders, surface active agents, thickeners, lubricants, preservatives e.g., methylhydroxybenzoate (including antioxidants), emulsifying agents, and the like. Any other therapeutic ingredient may comprise one or more of the following: antibiotic (e.g., antibacterial), antifungal and antiviral agents, and antihistamines (particularly peripherally acting antihistamines). However, when such other agent(s) are also present, according to another aspect of the invention, the compound of formula (1) or physiologically acceptable salt thereof and the other agent(s), need not necessarily be present as a pharmaceutical formulation as hereinbefore defined, but merely in combination or intimate admixture, i.e., optionally, a pharmaceutically acceptable carrier need not be present.

The combination with antihistamines is particularly favored for antiasthmatic use. Such an antihistamine may be selected from any compound described in European Patent Applications EP 0 859 949 A and EP 0 117 302 A. The amount and dosage regime for such an antihistamine may be chosen from any of those recited in the latter two European Specifications. Especially preferred are the antihistamines (E)-3-(6-(3-pyrrolidino)-1-(4-tolyl)prop-1E-enyl-(-2-pyridyl)) acrylic acid and (E)-3-(6-(3-pyrrolidino)-1-(4-tolyl)prop-1E-enyl(-2-pyridyl))propionic acid. Another preferred antihistamine is (E)-1-(4-methylphenyl)-1-(2-pyridyl)-3-pyrrolidinoprop-1-ene, otherwise known as typrolidine.

Also preferred is the antihistamine known as Seldane.

The compound of formula (I) and their salts may be prepared generally by the following processes and constitute a further aspect of the present invention.

For the preparation of compounds of the formula (I) wherein $R_1$ is 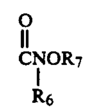 wherein $R_6$ and $R_7$ are as defined above, a compound of the formula (II)

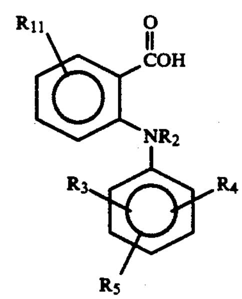

II wherein $R_2$, $R_3$, $R_4$, $R_5$, and $R_{11}$ are as defined above is converted to an acid chloride by treatment with oxalyl chloride, thionyl chloride, or the like to obtain the compound of formula (III)

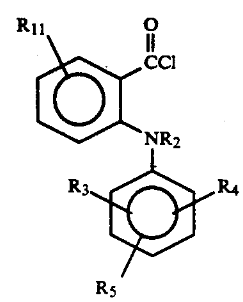

III wherein $R_2$ except not to be taken together with $R_1$, $R_3$, $R_4$, $R_5$, and $R_{11}$ are as defined above;

the compound of formula (III) is then treated with the appropriately substituted hydroxylamine of the formula (IV)

   IV to obtain the compound of formula (I) wherein $R_1$ is

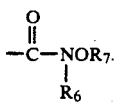

For the preparation of the compounds of formula (I) wherein $R_1$ is

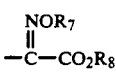

or wherein $R_1$ is taken together with $R_2$ and is

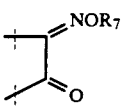

wherein $R_6$, $R_7$, $R_8$, and $L_1$ are as defined above;

(1) A compound of the formula (X)

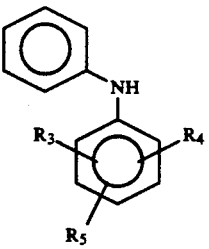   X is prepared by decarboxylating the compound of formula (II) wherein $R_2$ is hydrogen and $R_3$, $R_4$, $R_5$, and $R_{11}$ are as defined above; then (2) the compound of the formula (X) is treated with a compound of the formula

to obtain the compound of the formula (XI)

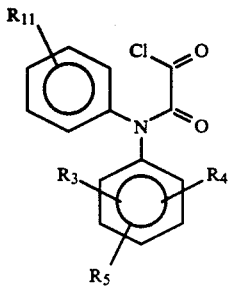   XI wherein $R_3$, $R_4$, $R_5$, and $R_{11}$ are as defined above; using conditions analogous to those in U.S. Pat. No. 4,092,430 then (3) the compound of formula (XI) is treated with a Lewis acid such as $AlCl_3$, $BF_3$, or the like, preferably $AlCl_3$; to cyclize the compound (XI) to the compound of the formula ($I_b$) wherein $L_2$ is oxygen which can optionally be further treated with a compound of the formula $H_2NOR_7$ wherein $R_7$ is as defined above; to obtain the compound of formula ($I''_b$)

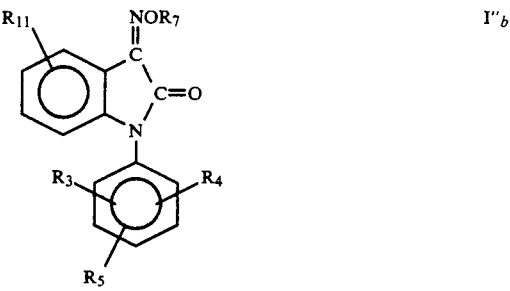   $I''_b$ which is then optionally treated with a nuceophile of the formula

wherein $R_8$ is H or alkyl to obtain the compound of the formula (I) wherein $R_1$ is

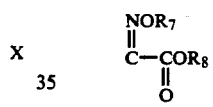

wherein $R_7$ is H, lower alkyl, or acyl and $R_8$ is hydrogen or lower alkyl.

Finally, for the preparation of the compounds of the formula (I) wherein $R_1$ taken together with $R_2$ is

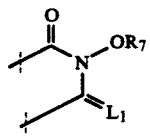

wherein $L_1$ is oxygen and $R_7$ is as defined above;

(i) a compound of the formula (I) wherein $R_1$ is

wherein $R_6$ is hydrogen is reacted with a compound of the formula

to obtain a compound of the formula (I) wherein $L_1$ is oxygen and $R_7$ is as defined above.

For the preparation of the compounds of formula I wherein $R_1$ taken together with $R_2$ is

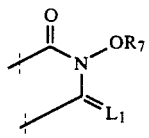

wherein $L_1$ is $H_2$ and $R_7$ is as defined above;

the compound of the formula (I) wherein $R_1$ is

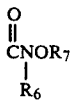

wherein $R_6$ is hydrogen and $R_7$ is as defined above may be reacted with formaldehyde to obtain the compound of the formula (I) wherein $R_1$ and $R_2$ together are

wherein $L_1$ is $H_2$ and $R_7$ is as defined above.

The above reactions are shown in the following Schemes I, II, and III followed by details for selected steps.

Scheme I

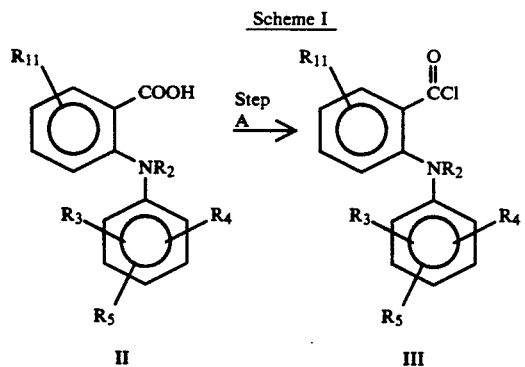

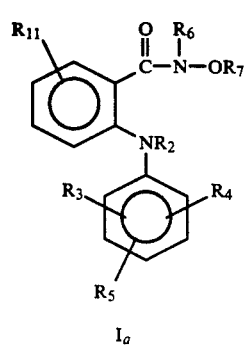

Scheme II

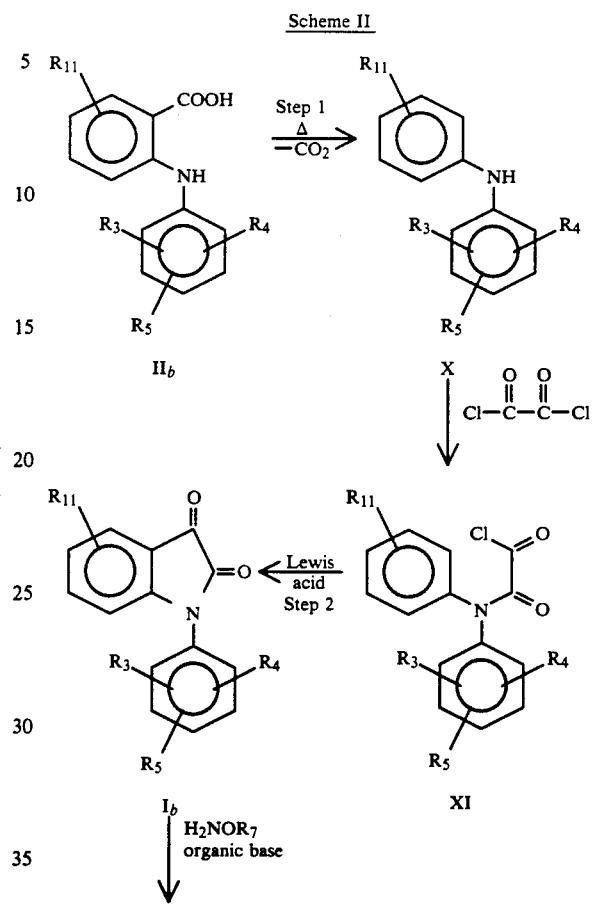

Scheme III

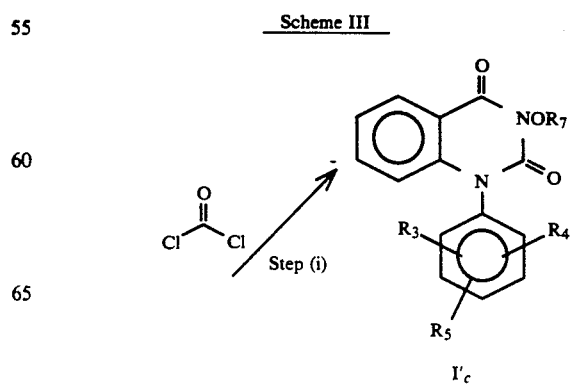

17
-continued
Scheme III
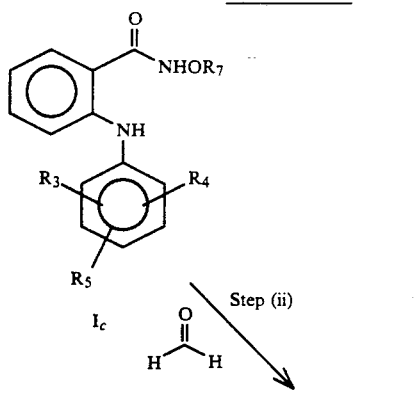
18
-continued
Scheme III
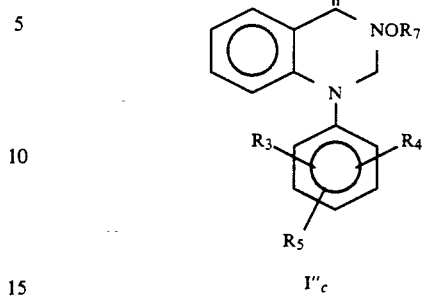
Scheme IV
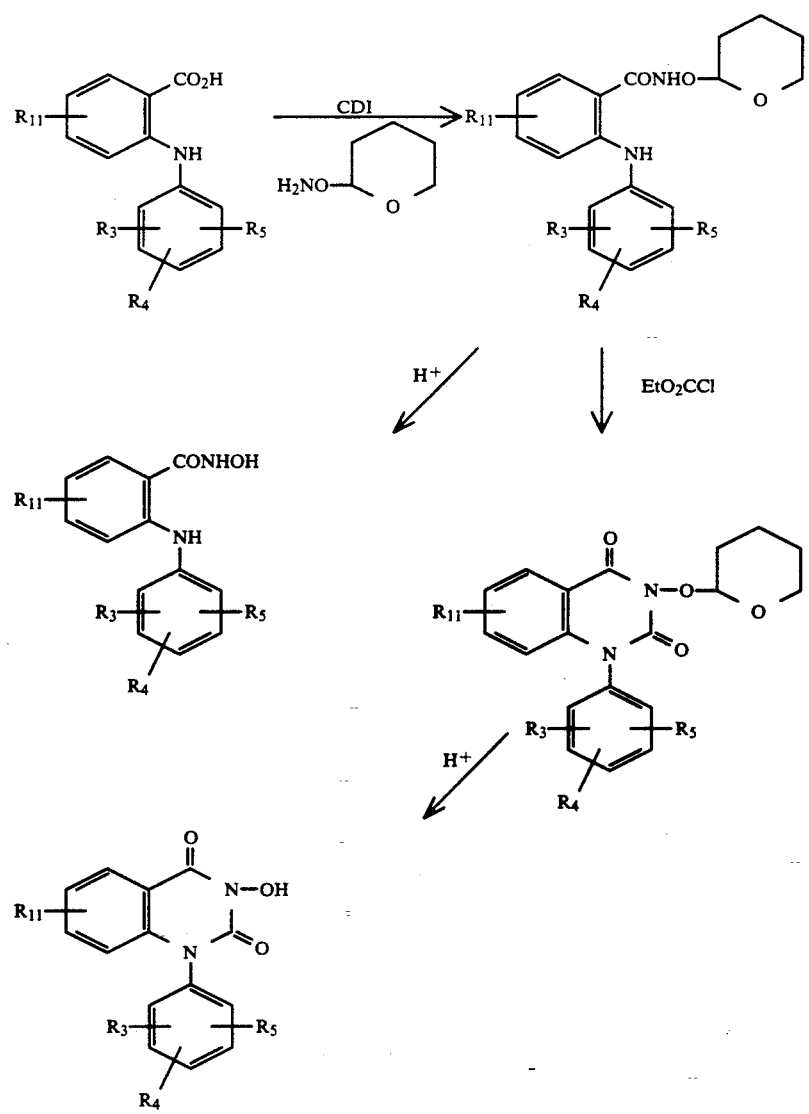
SCHEME I
Step A:
Treatment of the compound of formula II with oxalyl chloride/DMF affords the acid chloride of formula III, which is directly reacted with an appropriately substituted hydroxylamine HNR$_6$OR$_7$ to give rise to a compound of the formula I$_a$.

SCHEME II

Thermal decarboxylation of a compound of the formula II$_b$ by means of Cu/quinoline affords a compound of formula X, which is converted to the acid chloride of formula XI by treatment with oxalyl chloride. Cyclization of the compound of formula XI by means of a Lewis acid, preferably AlCl$_2$, then gives rise to a compound of formula I$_b$ (see reference in the literature to analogous reactions).

Conversion of the compound of formula I$_b$ to the corresponding oxime analogues of formula I$_b$ is performed by treating the compound of formula I$_b$ with an approximately substituted hydroxylamine and an organic base (preferably triethylamine).

Ring opening of the compound of formula I″$_b$ by means of hydroxide or alkoxide then affords a compound of formula I‴$_b$.

SCHEME III

The o-anilinohydroxamic acid of formula I$_c$ is treated with phosgene and an appropriate base according to a procedure analogous to such procedures in the literature to give the cyclic analogues of formula I′$_c$. Alternatively, treatment of the o-anilinohydroxamic acid of formula I$_c$ with formaldehyde under dehydrating conditions affords the cyclic analogues of formula I″$_c$.

SCHEME IV

The several reactions of this scheme show other means to prepare the compounds of the present invention using analogous methods well known in the art from starting materials that are known or can be readily prepared by known methods and variously exemplified hereinafter.

One of skill in the art would recognize variations in the sequence and would recognize appropriate reaction conditions from analogous reactions which may be appropriately used in the processes to make the compounds of formula (I) herein. Further, the starting materials are known or can be prepared by known methods.

Under certain circumstances it is necessary to protect either the N or O of intermediates in the above noted process with suitable protecting groups which are known. Introduction and removal of such suitable oxygen and nitrogen protecting groups are well-known in the art of organic chemistry; see for example "Protective Groups in Organic Chemistry," J. F. W. McOmie, ed., (New York, 1973), pages 43ff, 95ff, J. F. W. McOmie, *Advances in Organic Chemistry*, Vol. 3, 191-281 (1963); R. A. Borssonas, *Advances in Organic Chemistry*, Vol. 3, 159-190 (1963); and J. F. W. McOmie. *Chem. & Ind.*. 603 (1979).

Examples of suitable oxygen protecting groups are benzyl, t-butyldimethylsilyl, ethoxyethyl, and the like. Protection of an N—H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of the compounds of formula (I) described above are prepared by reacting the appropriate base or acid with a stoichiometric equivalent of the compounds of formula (I), respectively, to obtain pharmaceutically acceptable salts thereof.

The invention is further elaborated by the representative examples as follows. Such examples are not meant to be limiting.

EXAMPLES

Example 1

2-[(2,6-Dichloro-3-methylphenyl)amino]-N-hydroxy-N-phenylmethylbenzamide

Meclomen (5.92 g; 0.02 mol) is suspended in CH$_2$Cl$_2$ (150 ml) containing DMF (1.46 g, 0.02 mol) and cooled to 0° C. Oxalyl chloride is added to the solution over 30 minutes and the resulting yellow solution is stirred at 24° C. for 20 hours and then added to a cold solution of N-benzylhydroxylamine (2.46 g; 0.02 mol) in THF (60 ml)—H$_2$O (15 ml)—Et$_3$N (20 ml) mixture. The solution is allowed to come to 24° C. and treated with 2N HCl (160 ml). The product is extracted with CH$_2$Cl$_2$. The extracts are dried over sodium sulfate and evaporated to dryness. The residue is flash chromatographed through SiO$_2$ gel eluting with CH$_2$Cl$_2$. The fractions containing the product are evaporated and the solid residue is recrystallized from isopropylether/n-hexane yielding white crystals. Yield 1.45 g (18.6%); mp 133°–135° C.

EXAMPLE 2

Ortho-2,6-dichloro-3-methylanilinobenzhydroxamic acid or
2-[(2,6-dichloro-3-methylphenyl)amino]-N-hydroxybenzamide Ortho-2,6-dichloro-3-methylaniinobenzoic acid (3.0 g) is suspended in methylenechloride (75 ml) containing DMF (0.74 g). After cooling to 0° C., oxalyl chloride (2.8 g) is added dropwise. After the initial suspension dissolves, the solution is cannulated into an aqueous THF (125 ml THF/15 ml water) solution of hydroxylamine-HCl (2.8 g) and triethylamine (6.1 g). After stirring for thirty minutes at room temperature, the solution is then poured into 2 N aqueous HCl (300 ml). The organics are extracted into methylene chloride, dried (MgSO$_4$), and concentrated to afford a residue. Flash chromatography (230 mesh silica gel, 20% methylene chloride, 20% ethyl acetate, 60% hexane) affords 1.1 g (35% yield) of ortho-2,6-dichloro-3-methylanilinobenzhydroxamic acid, mp 170°–175° C.

Microanalysis: C, H, N,
Calc. C, 54.04; H, 3.89; N, 9.00,

Found C, 53.80; H, 3.74; N, 8.71.
Second run:
2-[(2,6-Dichloro-3-methylphenyl)amino]-N-hydroxybenzamide.

Yield: 23.35 g (62.6%); mp 158°–159° C., recrystallized from ether/n-hexane

The discrepancy in melting points between the first and second run appears to be a mechanical error in the first.

EXAMPLE 3

Ortho-2,6-dichloro-3-methylanilinobenz-N-methylhydroxamic acid or 2-[(2,6-dichloro-3-methylphenyl)amino]-N-hydroxy-N-methylbenzamide According to the procedure of Example 2, ortho-2,6-dichloro-3-methylanilinobenzoic acid (4.0 g) is reacted with N-methylhydroxylamine·HCl (4.5 g) to afford 2.1 g (47% yield) of ortho-2,6-dichloro-3-methylanilinobenz-N-methylhydroxamic acid, mp 117°–124° C.

Microanalysis: C, H, N.
Calc. C, 55.40; H, 4.34; N, 8.61.
Found C, 55.12; H, 4.55; N, 8.98.
Second run: Yield: 18.8 g (48%); mp 126°–128° C., recrystallized from ether/n-hexane.

EXAMPLE 4

Ortho-2,6-dichloro-3-methylanilinobenzhydroxamic acid O-methyl ether or
2 TM [(2,6-dichloro-3-methylphenyl)amino]-N-methoxybenzamide According to the procedure of Example 2, ortho-2,6-dichloro-3-methylaniiinobenzoic acid (3.0 g) is reacted with methoxylamine·HCl (3.4 g) to afford 2.0 g (61% yield) of ortho-2,6-dichloro-3-methylanilinobenzhydroxamic acid O-methyl ether, mp 210°–214° C.

Microanalysis: C, H, N.
Calc. C, 55.40; H, 4.34; N, 8.61.
Found C, 55.09; H, 4.21; N, 8.38.
Second run: Yield: 30.3 g (77.7%); mp 192°–194° C., recrystallized from ethyl acetate.

The following compounds are prepared following the procedures analogous to those of Example 1 above using appropriate starting materials.

EXAMPLE 5

2-[(2,6-Dichloro-3-methylphenyl)amino]-N-hydroxy-N1-methylethylbenzamide

Yield: 5.35 g (38%); mp 152°–153° C., recrystallized from acetonitrile.

EXAMPLE 6

2-[(2,3-dimethylphenyl)amino-N-hydroxy-N-methylbenzamide 1,1'-Carbonyl-diimidazole (5.35 g; 0.033 mol) is added to a solution of mefanamic acid (7.2% g; 0.03 mol) in dry DMF (100 ml). The solution is stirred at 24° C. for 20 hours and then briefly warmed to 50° C. N-Methylhydroxylamine hydrochloride (2.7 g; 0.032 mo) is added to the cooled solution at 24° C. and stirred for two days. The reaction mixture is then evaporated to dryness and the residue is taken up in CH$_2$Cl$_2$, washed with water, and dried over sodium sulfate and evaporated. The residue is flash chromatographed through silica gel and eluted with n-hexane-CH$_2$Cl$_2$-EtOAc (2:1:1) yielding a crude product which is rechromatographed through silica gel and eluted with n-hexane-CH$_2$Cl$_2$-EtOAc (4:5:1). The product is recrystallized from n-pentane to give white crystals. Yield 1.5 g (18.5%); mp 70°–71° C.

EXAMPLES 7-8

The following compounds are prepared following the procedures analogous to Example 6 as described above using appropriate starting materials.

2-[(2,3-Dimethylphenyl)amino]-N-methoxybenzamide

Yield: 6.5 g (48%); mp 151°–152° C., recrystallized from ethyl acetate.

2-(2,3-dimethylphenyl)amino]-N-hydroxy-N-(1-methylethyl)benzamide

Yield: 6.08 g (78.4%); mp 47°–49.5° C., recrystallized from n-pentane.

EXAMPLE 9

2-[(2,3-dimethylphenyl)amino]-N-hydroxybenzamide

Sodium methoxide (6.48 g; 0.12 mol) is added to a solution of mefanamic acid methyl ester (5.11 g; 0.02 mol) and hydroxylamine·HCl (5.56 g; 0.08 mol) in methanol (450 ml) and THF (50 ml). The mixture is heated to reflux for 20 hours. An additional amount of hydroxylamine·HCl (1.39 g; 0.02 mol) and sodium methoxide (1.62 g; 0.03 mol) is added and the heating is continued for an additional three hours. The reaction mixture is cooled and quenched with AcOH (60 ml), diluted with water (300 ml), and concentrated to half the original volume. It is extracted with CH$_2$Cl$_2$, washed with water, and dried over sodium sulfate. Evaporation of the solvent gives a solid residue which is recrystallized from ether - n-hexane to give an off-white solid. Yield 1.5 g (29.2%); mp 124°–125° C.

EXAMPLE 10

2-[(2,6-dichlorophenyl)amino]-N-hydroxybenzamide

According to the procedure of Example 1, 2-[(2,6-dichlorophenyl)amino]benzoic acid (J. S. Kaltenbronn, et al., *Arzneimittel-Forschung/ Drug Research*, 33(1), 4a, 621-627 (1983)) (4.1 g) is reacted with hydroxylamine hydrochloride (4.04 g) to provide 2-[(2,6-dichlorophenyl)amino]-N-hydroxybenzamide (2.9 g, 67%); mp 171-173° C.

Analysis:
Calc. C, 52.54; H, 3.40; N, 9.43; Cl, 23.86.
Found C, 52.26; H, 3.28; N, 9.39; Cl, 23.64.

EXAMPLE 11

N-hydroxy-2-(phenylamino)benzamide

A solution of N-phenylanthranilic acid (5.0 g, 23.4 mmol) and carbonyldiimidazole (5.7 g, 35.2 mmol) in dry THF (50 ml) is stirred for two hours at room temperature. O-THP-hydroxylamine (R. N. Warrener, *Angewardte Chemie*, Int. Ed. Engl. 5, 511 (1966)) (5.5 q, 46.8 mmol) is added and the reaction mixture is cooled, diluted with ethyl acetate (100 ml), and extracted with 0.1 N HCl (2×100 ml), saturated aqueous NaHCO$_3$ (100 ml), and brine (100 ml). The organic layer is dried (MgSO$_4$) and evaporated. The residue is purified by flash chromatography (silica, 10% CHCl$_3$/EtOAc). The crude, protected hydroxamate is dissolved in methanol (500 ml) and treated with 10 drops of concentrated HCl. The reaction mixture is stirred for 10 minutes at room temperature and the solvent is evaporated (temperature <35° C.). The washed with saturated aqueous NaHCO$_3$. The organic layer is dried (MgSO$_4$) and evaporated. Flash chromatography (silica, EtOAc) gives N-hydroxy-2-(phenylamino)benzamide (3.5 g, 65%, mp 97°-98° C. (from isopropyl ether/hexane).

Analysis $C_{13}H_{12}N_2O_2$:
Calc. C, 68.41; H, 5.30; N, 12.27.
Found C, 68.45; H, 5.27; N, 12.11.

The following compounds are prepared according to the procedure in Example 11 from the corresponding carboxylic acids (J. S. Kaltenbronn, et al., *Arzneimittel-Forschung/Drug Research*, 33(1), 4a, 621-627 (1983).

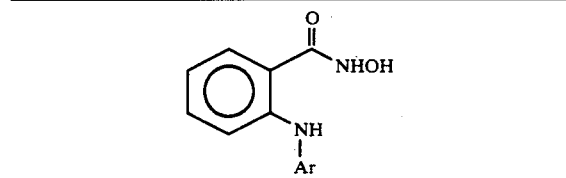

| Example Number | Ar | mp | % Yield |
|---|---|---|---|
| 12 | 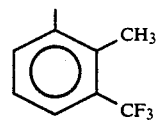 | 107–112° C. | 85% |
| 13 | 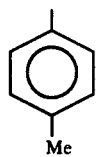 | amorphous foam | 84% |
| 14 | 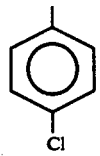 | amorphous foam | 94% |
| 15 | 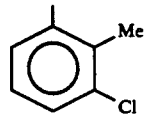 | 105–110° C. | 75% |
| 16 | 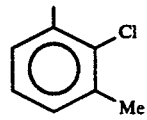 | 125–129° C. | 91% |
| 17 | 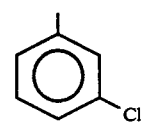 | amorphous foam | 86% |
| 18 | 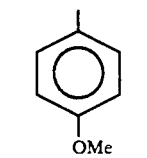 | amorphous foam | 86% |

-continued

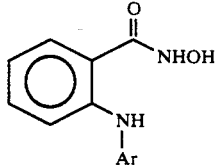

| Example Number | Ar | mp | % Yield |
|---|---|---|---|
| 19 | 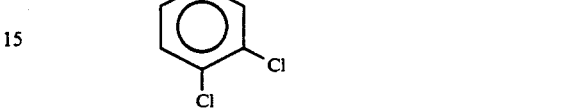 | 97–102° C. | 60% |
| 20 | 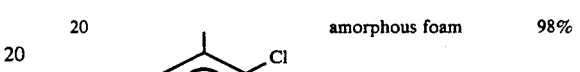 | amorphous foam | 98% |
| 21 | 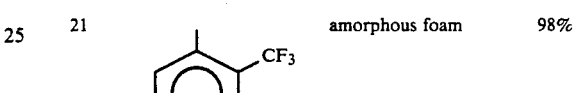 | amorphous foam | 98% |
| 22 | 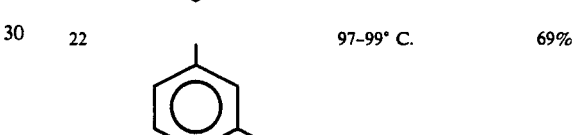 | 97–99° C. | 69% |
| 23 | 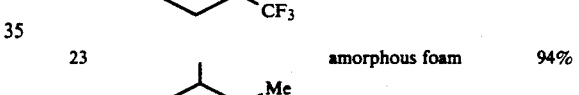 | amorphous foam | 94% |
| 24 |  | amorphous foam | 96% |

EXAMPLE 25

N-Hydroxy-N-Methyl-2-[(2,6-dichlorophenyl)amino]-benzamide

According to the procedure of Example 1, 2-(2,6-dichlorophenyl)amino]benzoic acid (2.0 g) is reacted with N-methylhydroxylamine hydrochloride (2.4 g) to afford N-hydroxy-N-methyl-2-[(2,6-dichlorophenyl)amino]benzamide (1.2 g, 54%), mp 137°–140° C.

Analysis $C_{14}H_{12}Cl_2N_2O_2$:
Calc. C, 54.04; H, 3.89; N, 9.00; Cl, 22.79.
Found C, 54.13; H, 3.90; N, 8.9g; Cl, 22.80.

EXAMPLE 26

2,3-Dihydro-3-hydroxy-1-phenyl-4(1H)quinazolinone

A mixture of N-hydroxy-2-(phenylamino)benzamide (1.4 g, 6.15 mmol), p-toluene sulfonic acid (400 ml), and paraformaldehyde (200 mg, 6.75 mmol) in toluene (50 ml) is stirred at room temperature for 30 minutes. The reaction mixture is heated for 10 minutes (in an oil bath preheated to 120°-130° C.) using a Dean-Stark trap to collect water. The reaction mixture is cooled and diluted with ethyl acetate (50 ml) and is extracted with saturated aqueous NaHCO$_3$ (4×50 ml) and water (50 ml). The organic layer is dried (MgSO$_4$) and evaporated. Recrystallization from EtOAc/hexane gives 0.6 g (40%) of 2,3-dihydro-3-hydroxy-1-phenyl-4(1H)-quinazolinone, mp 156°-160° C.

Analysis C$_{14}$H$_{12}$N$_2$O$_2$:
Calc. C, 69.99; H, 5.03; N, 11.66.
Found C, 69.66; H, 4.95; N, 11.70.

The following compounds are prepared according to the procedure of Example 26.

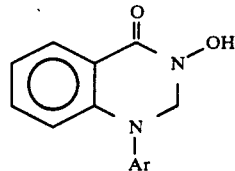

| Example Number | Ar | mp | % Yield | Prepared From Compound of | Molecular Formula |
|---|---|---|---|---|---|
| 27 | 2-CH$_3$, 3-CF$_3$ phenyl | 131-137° C. | 10% | Example 12 | C$_{16}$H$_{13}$F$_3$N$_2$O$_2$ |
| 28 | 4-Me phenyl | 162-164° C. | 22% | Example 13 | C$_{15}$H$_{14}$N$_2$O$_2$ |
| 29 | 4-Cl phenyl | 137-143° C. | 36% | Example 14 | C$_{14}$H$_{11}$ClN$_2$O$_2$ |
| 30 | 2-Me, 3-Cl phenyl | 130-134° C. | 15% | Example 15 | C$_{15}$H$_{13}$ClN$_2$O$_2$ |
| 31 | 2-Cl, 3-Me phenyl | 133-135° C. | 7.5% | Example 16 | C$_{15}$H$_{13}$ClN$_2$O$_2$ |
| 32 | 3-Cl phenyl | 128-133° C. | 19% | Example 17 | C$_{14}$H$_{11}$ClN$_2$O$_2$ |
| 33 | 4-OMe phenyl | 148-150° C. | 32% | Example 18 | C$_{15}$H$_{14}$N$_2$O$_3$ |

-continued

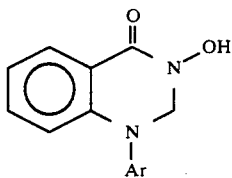

| Example Number | Ar | mp | % Yield | Prepared From Compound of | Molecular Formula |
|---|---|---|---|---|---|
| 34 | 3,4-diCl-phenyl | 179–182° C. | 28% | Example 19 | $C_{14}H_{10}Cl_2N_2O_2$ |
| 35 | 2,6-diCl-3-Me-phenyl | 197–200° C. | 22% | Example 2 | $C_{15}H_{12}Cl_2N_2O_2$ |
| 36 | 2,6-diCl-phenyl | 145–150° C. dec | 5% | Example 10 | $C_{14}H_{10}Cl_2N_2O_2$ |
| 37 | 2,3-diCl-phenyl | 135–137° C. | 27% | Example 20 | $C_{14}H_{10}Cl_2N_2O_2$ |
| 38 | 2-CF$_3$-phenyl | 166–168° C. | 28% | Example 21 | $C_{15}H_{11}F_3N_2O_2$ |
| 39 | 3-CF$_3$-phenyl | 133–135° C. | 19% | Example 22 | $C_{15}H_{11}F_3N_2O_2$ |
| 40 | 2,3-diMe-phenyl | 139–142° C. | 30% | Example 9 | $C_{16}H_{16}N_2O_2$ |
| 41 | 2-Me-phenyl | 174–176° C. | 15% | Example 23 | $C_{15}H_{14}N_2O_2$ |
| 42 | 3-Me-phenyl | 108–110° C. | 28% | Example 24 | $C_{15}H_{14}N_2O_2$ 0.1 $H_2O$ |

-continued

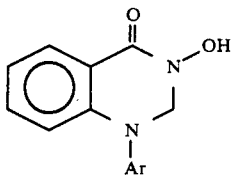

| Example Number | Ar | mp | % Yield | Prepared From Compound of | Molecular Formula |
|---|---|---|---|---|---|
| 43 | (2,6-dichloro-3-methylphenyl with OMe on N) | amorphous foam | 10 | Example 4 | $C_{16}H_{14}Cl_2N_2O_2$ |

EXAMPLE 44

1-(2,6-Dichloro-3-methylphenyl)-3-hydroxy-2,4-(1H,3H)quinazolinedione

2-[2,6-dichloro-3-methylphenyl]aminobenzoic acid (10.0 g) and DMF (2.5 g) are cooled to 0° C. in 200 ml $CH_2Cl_2$ under argon. Oxalyl chloride (9.4 g) is added dropwise at 0° C. When the initial slurry dissolves, the solution is cannulated into a THF solution of O-tetrahydropyranyl hydroxylamine (11.9 g) and triethylamine (20.5 g) at room temperature. The reaction is stirred at room temperature overnight. The solvent is evaporated and the residue is partitioned between ethyl acetate and saturated sodium bicarbonate. The organic layer is washed with saturated sodium bicarbonate and dried ($MgSO_4$). Evaporation gives a solid residue which is recrystallized from isopropyl ether to give 8 g of the O-tetrahydropyranyl hydroxamic acid, mp 148°–150° C. It is taken up in THF and treated with NaH (0.48 g) at 0° C. for 30 minutes. The reaction is warmed to room temperature and ethylchloroformate is added. After one hour, NaH (0.48 g) is added and the reaction is warmed to reflux for two hours. The reaction is quenched with water and extracted with ethyl acetate. The ethyl acetate layer is washed with brine and dried ($MgSO_4$). Evaporation of ethyl acetate gives 6.0 g of the 3-O-tetrahydropyranyl quinazolinedione. Two grams of the THP quinazolinedione is taken up in methanol and acidified to pH 1 with concentrated HCl. The reaction is stirred at room temperature overnight. The methanol is evaporated and the residue is taken up in ethyl acetate. It is washed with saturated sodium bicarbonate and dried ($MgSO_4$). The solvent is evaporated and the residue is recrystallized from isopropyl ether/hexane. Yield of 1-(2,6-dichloro-3-methylphenyl)-3-hydroxy-2,4-(1H,3H)-quinazolinedione =0.6 g (37%), mp 212°–213° C.

Analysis $C_{15}H_{10}Cl_2N_2O_3$:
Calc. C, 53.43; H, 3.00; N, 8.31; Cl, 21.03.
Found C, 53.49; H, 2.90; N, 8.22; Cl, 20.84.

EXAMPLE 45

1-(2,6-Dichloro-3-methylphenyl)-3-methoxy-2,4-(1H,3H)quinazolinedione 2-(2,6-Dichloro-3-methYlphenyl)amino-N-methoxybenzamide (1.6 %) is added to a THF (20 ml) solution of $NaHCO_3$ (0.14 g) and ethyl chloroformate (0.25 g) at −30° C. under argon. The reaction is allowed to stir overnight. The THF is evaporated and the residue is partitioned between diethyl ether and water. The organic layer is washed twice with water and brine after being dried over magnesium sulfate. The organic layer is concentrated to give a white solid, which is dissolved in THF and treated with sodium hydride at reflux for one hour under argon. The reaction is acidified with 1 N HCl and partitioned between ethyl acetate and water. The organic layer is washed with brine and dried ($MgSO_4$). The solvent is evaporated and the residue is adsorbed onto a silica gel pad. The pad is washed with chloroform to give the product. Recrystallization from $CH_2Cl_2/Et_2O$ gives 0.64 g (52% yield) of 1-(2,6-dichloro-3-methylphenyl)-3-methoxy-2,4-(1H,3H)-quinazolinedione, mp 211°–213° C.

Analysis $C_{16}H_{12}Cl_2N_2O_2$:
Calc. C, 54.72; H, 3.45; N, 7.98; Cl, 20.19.
Found C, 54.90; H, 3.54; N, 7.99, Cl, 20.16.

EXAMPLE 46

(2′,6′-Dichloro-3′-methyl)diphenylamine

A solution of meclofenamic acid (35 g) in quinoline (100 ml) with copper powder (3.0 g) is heated at reflux (bath temperature 240° C.) under an argon atmosphere for two hours. The reaction mixture is cooled and poured over ice water (350-ml). It is acidified by careful addition on concentrated HCl (85 ml) and extracted with ether. The organic layer is dried ($MgSO_4$) and evaporated. Flash chromatography (silica, $CH_2Cl_2$) followed by recrystallization from petroleum ether provides (2′,6′-dichloro-3′-methyl)diphenylamine (21 g, 69%), mp 77°–79° C.

EXAMPLE 47

1-(2,6-Dichloro-3-methylphenyl)-1H indole-2,3-dione

According to the procedure of A. Sallmann and R. Pfister (U.S. Pat. No. 4,092,430), a solution of (2',6'-dichloro-3'-methyldiphenylamine (20 g) and dimethylaminopyridine (390 mg) and oxalylchloride (15 ml) in chloroform (200 ml) is heated at reflux for 16 hours. The reaction mixture is cooled, evaporated, and redissolved in dichloroethane (150 ml). The resulting solution is added to a suspension of $AlCl_3$ (32 g) in dichloroethane. The reaction mixture is stirred at room temperature under an argon atmosphere for 20 hours. The reaction mixture is poured over ice water (500 ml) and the layers are separated. The aqueous layer is washed with $CHCl_3$ and the combined organic layers are evaporated. Chromatography (silica, $CHCl_3$) affords pure 1-(2,6-dichloro-3-methylphenyl)-1H-indole-2,3-dione (12.9 g, 53%), mp 164°–166° C.

EXAMPLE 48

1-(2,3-Dimethylphenyl)-1H-indole-2,3-dione and 6,7-Dimethyl-1-phenyl-lH-indole-2,3-dione According to the procedure of Example 47, (2',3'-dimethyl)diphenylamine (10 9) is reacted with oxalyl chloride to give a mixture of 1-(2,3-dimethyl-phenyl)-1H-indole-2,3-dione and 6,7-dimethyl-1-phenyl-1H-indole-2,3-dione. Flash chromatography (silica, CHCls) provides pure 1-(2,3-dimethylphenyl)-1H-indole-2,3-dione (0.82 %, 6%), mp 183°–187° C. and 6,7-dimethyl-1-phenyl-1H-indole-2,3-dione (4.4 g, 35%), mp 147°–149° C.

EXAMPLE 49

1-(2,6-Dichloro-3-methylphenyl)-lH-indole-2,3-dione-3-oxime

A solution of 1-(2,6-dichloro-3-methylphenyl)-1H-indole-2,3-dione (0.3 g) and hydroxylamine hydrochloride (0.07 g) in pyridine (2 ml) is stirred at room temperature for 20 minutes. The reaction mixture is diluted with ethyl acetate (20 ml) and washed with 1 N HCl ($2 \times 100$ ml). The organic layer is dried ($MgSO_4$) and evaporated. Flash chromatography (silica, $CH_2Cl_2$) followed by recrystallization from isopropyl ether affords 1-(2,6-dichloro-3-methylphenyl)-1H-indole-2,3-dione 3-oxime (256 mg, 80%), mp 190°–191° C.

Analysis $C_{15}H_{10}Cl_2N_2O_2$:
Calc. C, 56.10; H, 3.14; N. 8.72: Cl, 22.08.
Found C, 56.20; H, 3.12; N, 8.76; Cl, 22.0.

EXAMPLE 50

6,7-Dimethyl-1-phenyl-1H-indole-2,3-dione-3-oxime

According to the procedure of Example 49, 6,7-dimethyl-1-phenyl-1H-indole-2,3-dione (2 g) is converted to 6,7-dimethyl-1-phenyl-1-H-indole-2,3-dione-3-oxime (1.2 g, 56%), mp 245°–250° C. dec.

Analysis $C_{16}H_{14}N_2O_2$:
Calc. C, 72.16; H, 5.30; N, 10.52.
Found C, 71.78; H, 5.25; N, 10.41.

EXAMPLE 51

1-(2,3-Dimethylphenyl)-lH-indole-2,3-dione-3-oxime

According to the procedure of Example 49, 1-(2,3-dimethylphenyl)-1H-indole-2,3-dione (0.65 g), is converted to-1-(2,3-dimethylphenyl)-1H-indole-2,3-dione-3-oxime (0.5 g, 63%), mp 215°–216° C.

Analysis $C_{16}H_{14}N_2O_2$:
Calc. C, 72.16; H, 5.30; N, 10.52.
Found C, 71.92; H, 5.07; N, 10.51.

EXAMPLE 52

2-[(2,6-Dichloro-3-methylphenyl)amino]-a-(hydroxylimino)benzene acetic acid

A solution of 1-(2,6-dichloro-3-methylphenyl)-1H-indole-2,3-dione-3-oxime (2.25 9) in 6 N NaOH (10 ml) and 4 ml MeOH is heated at 50° C. for two days without a reflux condenser. The resulting residue is taken up in water (50 ml) and filtered. It is neutralized with 1 N HCl with ice bath cooling. The precipitate is collected by filtration. The residue is air dried, dissolved in ether, and filtered. 2-[(2,6-Dichloro-3-methylphenylamino]-α-(hydroxylimino)-benzeneacetic acid (0.28 g, 50%) is precipitated from the ether solution by the addition of hexane, mp 152°–154° C. dec.

The usefulness of the compounds of the present invention as inhibitors of the 5-lipoxygenase enzyme, cyclooxygenase, or other related biochemical actions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmuno assay (RIA) kits of $LTB_4$ and $PGF_{2\alpha}$ were obtained from Amersham (Arlington Heiqhts, Ill.) and Seragen (Boston, Mass.) respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 %; $Na_2HPO_4$, 1.15 g; $KH_2PO_4$, 0.2 g; and KCl, 0.2 g/l). Cells are finally suspended in PBS containing 1.0 mM calcium at a density of $2 \times 10^6$ cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at −20°. Aliquots (100 μl) are analyzed for $LTB_4$ and $PGF_{2\alpha}$ using radioimmuno assay kits as provided by the supplier.

Table 1 contains biochemical data obtained from this whole cell assay as $IC_{50}$s which are calculated as the amount of test compound causing 50% inhibition of $LTB_4$ or $PGF_{2\alpha}$ formation.

TABLE 1

| Entry | $ARBL^{a,b}$ | $ARBC^{a,c}$ |
|---|---|---|
| Example 2 | 3.9 | 1.1 |
| Example 3 | 1.5 | 15.0 |
| Example 4 | 16.0 | 0.55 |

TABLE 1-continued

| Entry | ARBL[a,b] | ARBC[a,c] |
|---|---|---|
| Example 10 | 88% @ 16 μM | 80% @ 16 μM |
| Example 9 | 1.8 | 60% @ 0.5 μM |
| Example 35 | 3.2 | 2.2 |
| Example 49 | 6.5 | 28 |
| Meclomen | 24.0 | 0.10 |

[a]Data are expressed as IC$_{50}$ values (μM) for inhibition of substrate conversion to product.
[b]IC$_{50}$ for LTB$_4$ inhibition.
[c]IC$_{50}$ for PGF$_{2\alpha}$ inhibition.

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield, N.J.) in 10 ml of sterile saline (0.9%) solution (Travenol). The solution is vortexed for 30 to 45 minutes. Animals are dosed with compound one hour before carrageenan challenge. Foot paw edema is induced by injecting 0.05 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured five hours after carrageenan. The difference between the five-hour and the initial paw volume is expressed as delta edema. The delta edema for each test group of animals is used to calculate the percent inhibition of edema achieved by the compound at the test dose compared with the vehicle control group. The ID$_{25}$ (the dose at which swelling is inhibited by 25%) was calculated by probit analysis for the dose at which a result of 25 percent inhibition occurs.

Mycobacterium—Induced Rat Footpad Edema Assay (MFE): Protocol

*Myobacterium butyricum* (5 mg/ml) is suspended in paraffin oil by sonication for ten minutes in an ice bath. Footpad edema is induced on Day 0 by injecting 0.1 ml of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle one hour before Myobacterium injection and on Days 1 and 2. Inhibition of swelling is determined by comparing the change in hindpaw volume in compound- and vehicle-treated rats. An ID*c (the dose at which swelling is inhibited by 40%) was calculated by probit analysis.

Gastric Ulcerogenicity (UD) Protocol

Male outbred Wistar rats (100–250 gms) were fasted for 24 hours. After fasting, test compounds were administered orally (in 2 ml/kg of 0.5% hydroxypropyl methylcellulose) and the rats were denied access to food and water for six more hours. The rats were then sacrificed with CO$_2$ so that the stomachs could be removed, opened along the greater curvature, and evaluated for the presence of gastric ulcers. Results are expressed as the percent of rats with gastric ulcers at a given dose.

The results of the CFE-2, MFE, and UD assays for each of the noted compounds is shown in the following Table 2.

TABLE 2

| | In Vivo Pharmacology | | |
|---|---|---|---|
| Entry | CFE-2[a] | MFE[b] | UD$_{50}$[c] |
| Example 1 | T[d] | 27.0 | N @ 200 |
| Example 2 | 0.2 | 2.5 | N @ 200 |
| Example 3 | 1.3 | 24.0 | N @ 200 |
| Meclomen | 8.2 | 0.39 | 36.0 |

[a]ID$_{25}$ in mg/kg PO.
[b]ID$_{40}$ in mg/kg PO.
[c]Dose in mg/kg PO which produces a 50% occurrence of ulcers in rats. N is 0% of rats have ulcers occurring at 200 mg.
[d]Assay was not validated by standard.

Accordingly, the present invention is (a) a compound of formula (I) or an acid addition or base addition salt thereof;

(b) a method for preparing a compound of formula (I) or a pharmacologically acceptable acid addition or base salt thereof;

(c) a pharmaceutical formulation comprising a compound of formula (I) or a physiologically acceptable salt thereof and a pharmaceutically acceptable carrier therefor;

(d) a method for preparing such formulations;

(e) a method for the inhibition of the lipoxygenase and/or cyclooxygenase pathways of the arachidonic acid metabolism by use of a nontoxic, effective, inhibitory amount of a compound of formula (1) or a physiologically acceptable sat thereof;

(f) a method for the prophylaxis or treatment of disease in a mammal, including man, comprising the administration to said mammal of a nontoxic, therapeutically or prophylactically effective amount of a compound of formula (I) or a physiologically acceptable salt thereof;

(g) a method for the prophylaxis or treatment of any individual condition described herein, in a mammal, including man, comprising the administration to said mammal of a nontoxic therapeutically or prophylactically effective amount of a compound of formula (I) or a physiologically acceptable salt thereof;

(h) a method for the prophylaxis or treatment of asthma in a mammal, including man, comprising administration to said mammal of a nontoxic, effective, anti-asthmatic amount of a compound of formula (1) or a physiologically acceptable salt thereof;

(i) a compound of formula (I) or a physiologically acceptable salt thereof for use in medicine, especially as defined in (f)–(h) above;

(j) use of a compound of formula (I) or a physiologically acceptable salt thereof in the manufacture of medical therapeutic agents, particularly those for use as defined in (f)–(h) above; and (k) any novel feature described herein.

We claim:

1. A compound of the formula (I)

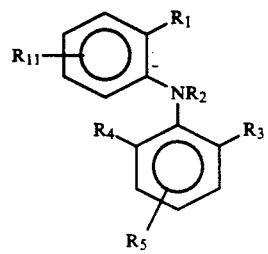

and pharmaceutically acceptable salt thereof;
(1) wherein $R_1$ is (i)

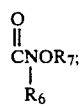

(ii)

wherein $R_6$ is hydrogen, lower alkyl, aryl, aralkyl, or cycloalkyl of from three to ten carbons having three to seven ring carbons; $R_7$ is H, lower alkyl, or acyl, and $R_8$ is H or lower alkyl or (iii) as defined together with $R_2$ below;

(2) $R_2$ is hydrogen, lower alkyl, or taken together with $R_1$ is

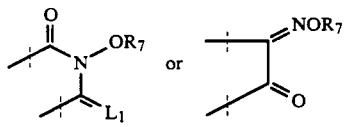

wherein $L_1$ is $H_2$ or oxygen; and $R_7$ is independently as defined above;

(3) $R_5$ and $R_{11}$ are independently H, fluoro, chloro, bromo, trifluoromethyl, lower alkyl, CN, hydroxy, lower alkoxy, $-S(O)_n$-lower alkyl wherein n is an integer or 0 through 2, $NO_2$, or $NR_9R_{10}$ wherein $R_9$ or $R_{10}$ are independently hydrogen, lower alkyl, or acyl; and $R_3$ and $R_4$ are fluoro, chloro, bromo, trifluoromethyl, or lower alkyl; with a proviso that when $R_1$ is

then $R_3$ and $R_4$ cannot both be lower alkyl when $R_5$ is hydrogen, and when $R_1$ is

wherein $R_7$ is hydrogen or lower alkyl and one of $R_3$ or $R_4$ is lower alkyl then $R_5$ cannot be meta-nitro, meta-difluoromethyl, or meta-trifluoromethyl when $R_{11}$ is H, Br, Cl, or nitro.

2. A compound of claim 1 wherein $R_{11}$ is hydrogen or lower alkyl.

3. A compound of claim 1 which is 2-[(2,6-dichloro-3-methylphenyl)amino]-N-hydroxybenzamide.

4. A compound of claim 1 which is 2-[(2,6-dichloro-3-methylphenyl)amino] TM N-methoxybenzamide.

5. A compound of claim 1 which is 2-[(2,6-dichloro-3-methylphenyl)amino-N-hydroxy-N-methylbenzamide.

6. A compound of claim 1 which is 2-[(2,6-dichloro-3-methylphenyl)amino]-N-hydroxy-N-phenylmethylbenzamide.

7. A compound of claim 1 which is 2-[(2,6-dichloro-3-methylpheny)amino]-N-hydroxy-N-(1-methylethylbenzamide.

8. A compound of claim 1 which is 2-[(2,6-dichlorophenyl)amino]-N-hydroxybenzamide.

9. A compound of claim 1 which is N-hydroxy-N-methyl-2[(2,6-dichlorophenyl)amino]benzamide.

10. A compound of claim 1 which is 1-(2,6-dichloro-3-methylphenyl)-2,3-dihydro-3-hydroxy-4(1H)-quinazolinone or the monosodium salt thereof.

11. A compound of claim 1 which is 1-(2,6-dichlorophenyl)-2,3-dihydro-3-hydroxy-4(1H)-quinazolinone.

12. A compound of claim 1 which is 1-(2,6-dichloro-3-methylphenyl)-3-methoxy-4(1H)-quinazolinone.

13. A compound of claim 1 which is 1-(2,6-dichloro-3-methylphenyl)-3-hydroxy-2,4-(1$\underline{H}$,3$\underline{H}$)-quinazolinedione.

14. A compound of claim 1 which is 1-(2,6-dichloro-3-methylphenyl)-3-methoxy-2,4-(1$\underline{H}$,3$\underline{H}$)-quinazolinedione.

15. A compound of claim 1 which is 1-(2,6-dichloro-3-methylphenyl)-1H-indole-2,3-dione-3-oxime.

16. A compound of claim 1 which is 2-[(2,6-dichloro-3-methylphenyl)amino]-α-(hydroxylimino)benzene acetic acid.

17. A pharmaceutical composition for inhibiting 5-lipoxygenase or cyclooxygenase which comprises an amount effective for inhibiting 5-lipoxygenase or cyclooxygenase of a compound as claimed in claim 16, together with a pharmaceutically acceptable carrier.

* * * * *